United States Patent
Bender et al.

(10) Patent No.: US 10,943,477 B2
(45) Date of Patent: Mar. 9, 2021

(54) DYNAMICALLY DEFINING A SAFETY ZONE AROUND A USER

(71) Applicant: INTERNATIONAL BUSINESS MACHINES CORPORATION, Armonk, NY (US)

(72) Inventors: Michael Bender, Rye Brook, NY (US); Kevin C. McConnell, Austin, TX (US); Carol Ann Zichi, Ada, MI (US); Gregory J. Boss, Saginaw, MI (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 308 days.

(21) Appl. No.: 15/866,758

(22) Filed: Jan. 10, 2018

(65) Prior Publication Data
US 2019/0213881 A1    Jul. 11, 2019

(51) Int. Cl.
*G08G 1/0967* (2006.01)
*H04W 4/021* (2018.01)
(Continued)

(52) U.S. Cl.
CPC ....... *G08G 1/096725* (2013.01); *B60W 50/14* (2013.01); *G08G 1/096775* (2013.01);
(Continued)

(58) Field of Classification Search
CPC . G08G 1/096725; G08G 1/166; B60W 50/14; H04W 4/021; A61B 5/0002; H04L 67/12
(Continued)

(56) References Cited

U.S. PATENT DOCUMENTS

| 5,314,037 A | 5/1994 | Shaw et al. |
| 8,354,942 B2 | 1/2013 | Stahlin |

(Continued)

FOREIGN PATENT DOCUMENTS

WO    2016087928    6/2016

OTHER PUBLICATIONS

Mullis, "Entering the Safety Zone: How IoT can Improve Construction Sites", https://hpe-enterpriseforward.com/entering-safety-zone-iot-can-improve-construction-sites/, HPE Enterprise, Jan. 11, 2016, 2 pages.
(Continued)

*Primary Examiner* — Marthe Y Marc-Coleman
(74) *Attorney, Agent, or Firm* — Jay Wahlquist; Andrew D. Wright; Roberts Calderon Safran & Cole, P.C.

(57) ABSTRACT

Systems and methods for dynamically defining a safety zone around a user are disclosed. In embodiments, a computer-implemented method comprises: receiving, by a computing device, real-time safety data including a location of a remote participant device of a user; receiving, by the computing device, real-time driving event data from a remote vehicle; determining, by the computing device, a spatial safety zone for the remote participant device based on the real-time safety data and the real-time driving event data; determining, by the computing device, that the remote vehicle has entered the spatial safety zone; and sending, by the computer device, safety information regarding the user to the remote vehicle based on the remote vehicle entering the spatial safety zone.

20 Claims, 6 Drawing Sheets

(51) Int. Cl.
*B60W 50/14* (2020.01)
*G08G 1/16* (2006.01)
*H04L 29/08* (2006.01)
*A61B 5/00* (2006.01)

(52) U.S. Cl.
CPC ............ *G08G 1/166* (2013.01); *H04W 4/021* (2013.01); *A61B 5/0002* (2013.01); *H04L 67/12* (2013.01)

(58) Field of Classification Search
USPC .......................................................... 701/117
See application file for complete search history.

(56) References Cited

U.S. PATENT DOCUMENTS

| | | | |
|---|---|---|---|
| 8,983,771 | B2 | 3/2015 | Breed |
| 9,204,261 | B2 | 12/2015 | Mukaiyama |
| 9,358,940 | B2 | 6/2016 | Cooper et al. |
| 9,386,401 | B2 | 7/2016 | Gold |
| 2008/0147277 | A1 | 6/2008 | Lu et al. |
| 2011/0090093 | A1 | 4/2011 | Grimm et al. |
| 2011/0288774 | A1* | 11/2011 | Bengtsson ............... G08G 1/16 701/301 |
| 2012/0025964 | A1* | 2/2012 | Beggs .................. B60Q 1/2673 340/435 |
| 2013/0144490 | A1 | 6/2013 | Lord et al. |
| 2014/0324268 | A1 | 10/2014 | Montemerlo et al. |
| 2015/0032288 | A1* | 1/2015 | Huth ..................... B60W 30/08 701/1 |
| 2015/0073438 | A1* | 3/2015 | Levy ...................... A45D 44/22 606/131 |
| 2015/0274165 | A1* | 10/2015 | von Collani ........ B60W 30/143 701/70 |
| 2016/0075332 | A1* | 3/2016 | Edo-Ros .................. B60T 7/22 701/70 |
| 2016/0357188 | A1 | 12/2016 | Ansar |
| 2017/0061203 | A1* | 3/2017 | Takatani ............ G06K 9/00805 |
| 2017/0131712 | A1 | 5/2017 | Ricci et al. |

OTHER PUBLICATIONS

Lamagna, "Building the Next-Generation Car with Intel IoT", http://blogs.intel.com/iot/2015/11/23/building-the-next-generation-car-with-intel-iot/, Intel, Nov. 23, 2015, 6 pages.

Anonymous, "Technology—Geofencing, Location Marketing", http://bluedotinnovation.com /technology, Blue Dot Innovation, accessed Oct. 20, 2017, 6 pages.

* cited by examiner

DYNAMICALLY DEFINING A SAFETY ZONE AROUND A USER

BACKGROUND

The present invention relates generally to safety systems for vehicles and, more particularly, to dynamically defining spatial safety zones around participants.

Many states have laws relating to vehicles changing lanes or slowing down to avoid emergency vehicles on the side of a road, but such laws cannot cover every possible scenario in which it would be desirable for a vehicle to drive with additional caution or to slow down. For example, the presence of pedestrians on a local street (with or without sidewalks) is reason in itself for a vehicle to slow down; and the rate of speed of the vehicle should be adjusted based on surrounding conditions. The presence of a bicyclist sharing the road with a vehicle, or another vehicle pulled over on a highway or changing a flat tire, provide more reasons for a driver of the vehicle to drive with caution. Each of these scenarios calls for a different optimal vehicle speed.

Some systems have been developed to attempt to address safety concerns by providing vehicles with sensors to detect obstacles, such as other vehicles or pedestrians, and provide a driver with a warning. Other systems have been developed to enable vehicles to share data regarding hazards, such as surface conditions of a road.

SUMMARY

In an aspect of the invention, a computer-implemented method includes: receiving, by a computing device, real-time safety data including a location of a remote participant device of a user; receiving, by the computing device, real-time driving event data from a remote vehicle; determining, by the computing device, a spatial safety zone for the remote participant device based on the real-time safety data and the real-time driving event data; determining, by the computing device, that the remote vehicle has entered the spatial safety zone; and sending, by the computer device, safety information regarding the user to the remote vehicle based on the remote vehicle entering the spatial safety zone.

In another aspect of the invention, there is a computer program product for dynamically defining a safety zone around a user. The computer program product comprises a computer readable storage medium having program instructions embodied therewith. The program instructions are executable by a computing device to cause the computing device to: send real-time safety data regarding a participant device to a remote central server, the real-time safety data including a location of the participant device; receive a safety notification from the central server, the safety notification including a defined spatial safety zone about the participant device; and broadcast a safety signal based on the safety notification, wherein the safety signal is configured to be detected by one or more sensors of a vehicle.

In another aspect of the invention, there is a system for dynamically defining a safety zone around a user. The system includes a CPU, a computer readable memory and a computer readable storage medium associated with a computing device; program instructions to receive real-time safety data including a location of a remote participant device of a user; program instructions to receive real-time driving event data from a remote vehicle, the real-time driving event data including a speed of the remote vehicle; program instructions to determine a spatial safety zone based on the real-time safety data and the real-time driving event data; and program instructions to send a safety notification to the participant device, the safety notification causing a safety signal to be broadcast from the participant device based on the spatial safety zone, wherein the program instructions are stored on the computer readable storage medium for execution by the CPU via the computer readable memory.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

Figure 1:
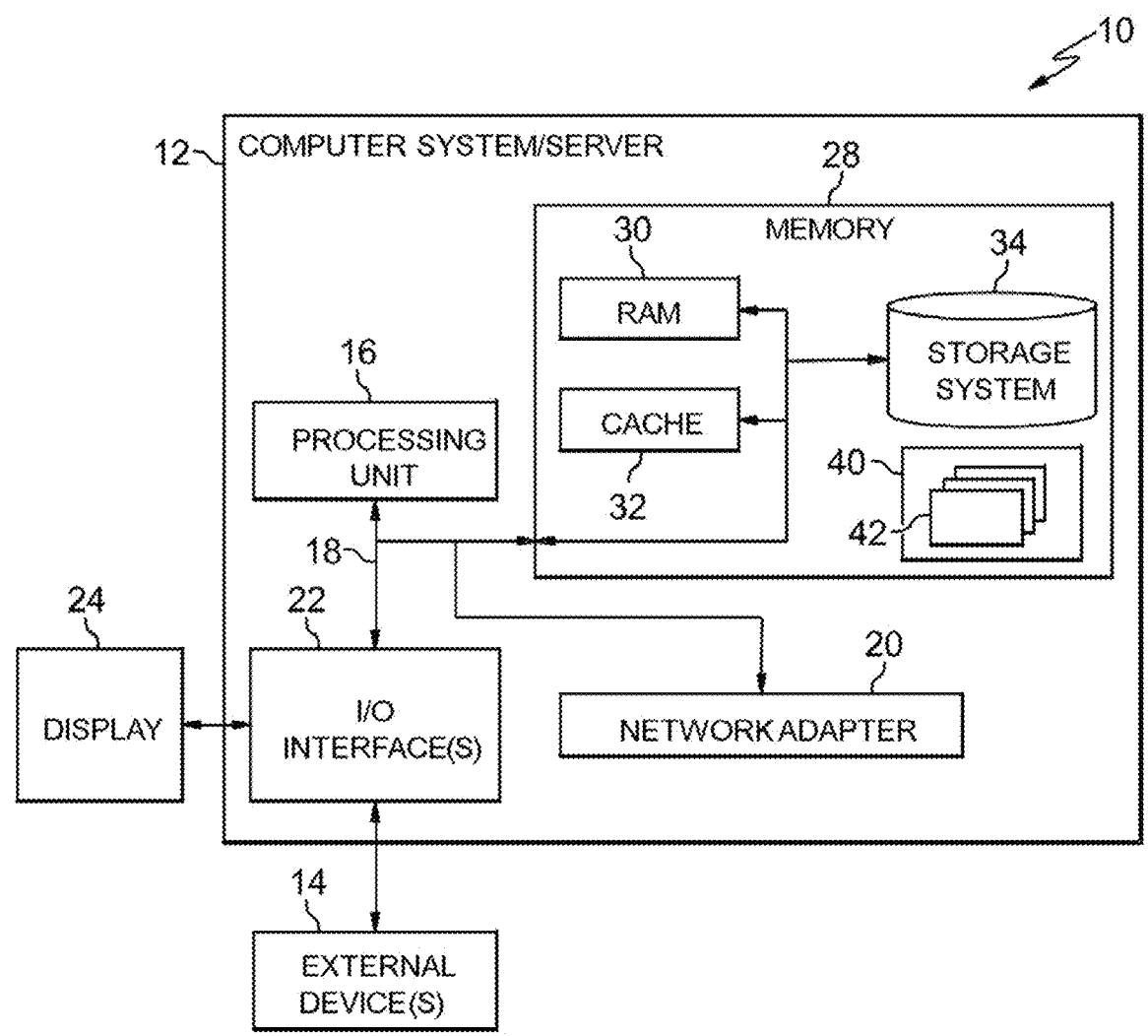
FIG. 1 depicts a computing infrastructure according to an embodiment of the present invention.

The present invention relates generally to safety systems for vehicles and, more particularly, to dynamically defining spatial safety zones around participants. Embodiments of the invention define a safety zone (spatial safety zone) around pedestrians or other participants needing protection by directing vehicles to slow down when in the vicinity of the participant(s) when collision risks are high. In aspects, a central server is provided for registering participants (e.g., a person or animal), internet of things (IoT) devices (e.g., smartphones, personal wearable devices, etc.) and vehicles. In aspects, the central server is configured to know if a participant device is attached to a person, animal, child or vehicle, for example. Registered IoT devices may be global positioning system (GPS) enabled, and may provide safety data including location data, acceleration data, and speed data to the central server. Based on location based parameters (e.g., the location of the participant device, type of street, local laws, etc.), real-time safety data received from the participant device, and driving data received from nearby vehicles, the central server may dynamically determine a safety zone around a participant device, as well as a target vehicle speed.

In embodiments, a central-server-based system is provided whereby a central server acts as an intermediator of safety data between IoT devices and vehicles (e.g., smart vehicles, self-driving vehicles, etc.). In such cases, the central server determines a safety zone around a participant device and communicates safety data to a nearby vehicle, such as a warning to slow down or instructions to automatically cause the vehicle to decelerate. In aspects, a vehicle receives safety information regarding a target speed of the vehicles, wherein the target speed changes dynamically based on the position of the vehicle with respect to the participant device (e.g., the target speed is lower the closer the vehicle gets to the participant device), as sensed by the central server. In aspects, the central server receives a notification of an emergency from the participant device (e.g., a participant is changing a tire, a participant has fallen on a street) and calculates a target speed of one or more nearby vehicles based on the emergency. In embodiments, safety information received at a vehicle from a central server causes the vehicle to display target speed limits, or to automatically change speed based on the target speed limits. In embodiments, the central server identifies physical structures, such as fences, buildings or other physical barriers between a participant device and a vehicle, and utilizes the information when determining a safety zone and target speed around the participant device (e.g., a fence would prevent a child from running into the street, and therefore, the target speed of a vehicle on an opposite side of the fence from the child may not be affected by the presence of a participant device of the child). Additional safety information that may be utilized by the central server includes average braking speed of a nearby vehicle, weather conditions, and road conditions.

In alternative embodiments, a participant device-based system is provided whereby the participant device acts as an intermediator of safety data between a central server and a plurality of vehicles. In such cases the central server determines a safety zone around a participant device and communicates instructions to the participant device to broadcast a safety signal configured to be detected by nearby vehicles. In aspects, nearby vehicles sense the safety signal broadcast by the participant device and respond accordingly (e.g., warn a driver of the vehicle to slow down, automatically cause the vehicle to decelerate, etc.).

Advantageously, embodiments of the present invention provide improvements to participant devices and vehicle computing devices by adding safety functions that leverage data from a network of computing devices. Moreover, embodiments of the invention enable the generation of safety signals configured to be sensed by nearby vehicles, as well as the generation of safety information to initiate changes in vehicles as they approach a participant (e.g., another vehicle, a bicycle, a pedestrian, an animal, etc.). Other benefits of the present invention will become apparent from the discussion below.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring now to FIG. 1, a schematic of an example of a computing infrastructure is shown. Computing infrastructure 10 is only one example of a suitable computing infrastructure and is not intended to suggest any limitation as to the scope of use or functionality of embodiments of the invention described herein. Regardless, computing infrastructure 10 is capable of being implemented and/or performing any of the functionality set forth hereinabove.

In computing infrastructure 10 there is a computer system (or server) 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system executable instructions, such as program modules, being executed by a computer system. Generally, program modules may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system 12 in computing infrastructure 10 is shown in the form of a general-purpose computing device. The components of computer system 12 may include, but are not limited to, one or more processors or processing units (e.g., CPU) 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/

Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc.

Figure 2:
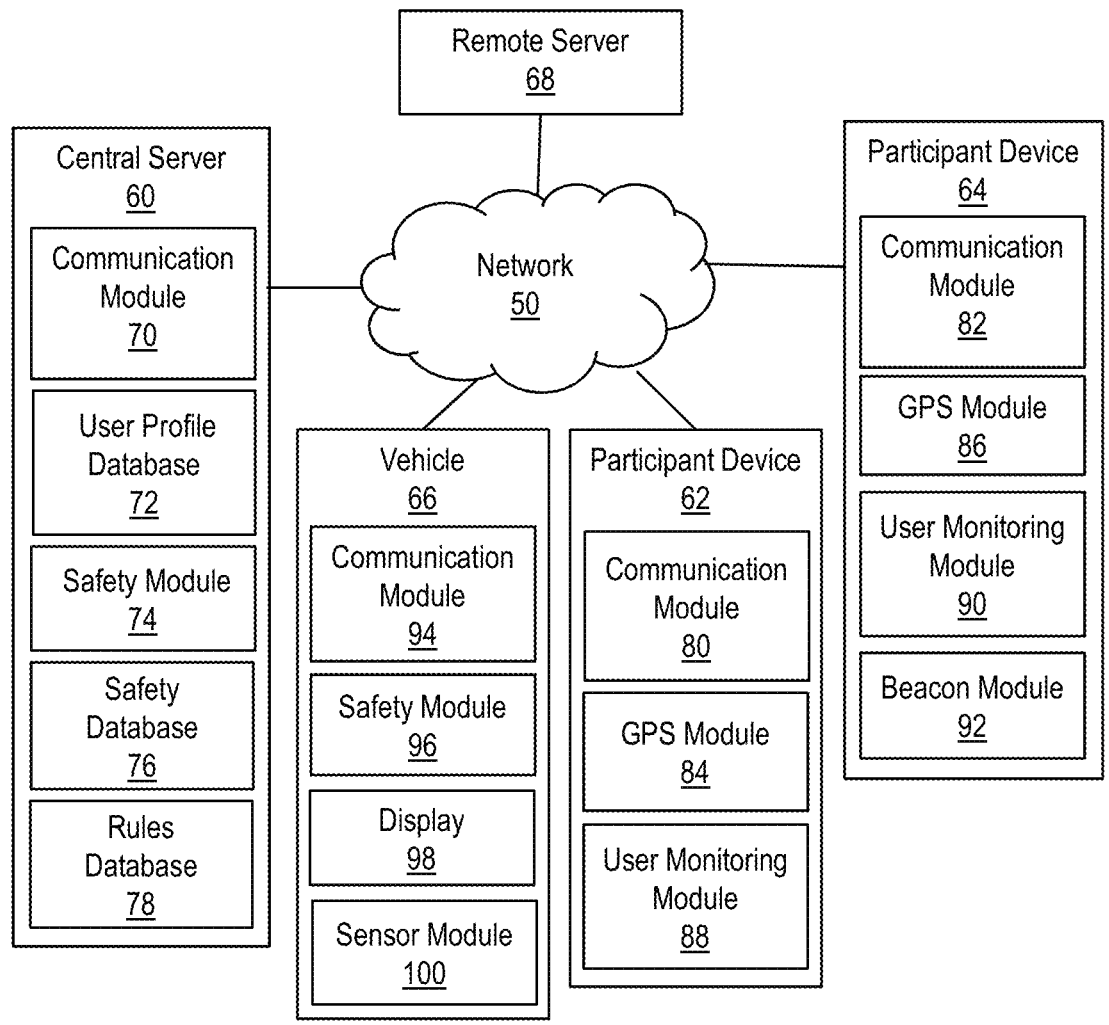
FIG. 2 shows an exemplary environment in accordance with aspects of the invention.

FIG. 2 shows an exemplary environment in accordance with aspects of the invention. The environment includes a network 50 connecting a central server 60 with one or more participant devices indicated at 62 and 64 remote from the central server 60, as well as one or more vehicles represented at 66 remote from the central server, and one or more remote server represented at 68. The central server 60 may comprise a computer system 12 of FIG. 1, and may be connected to the network 50 via the network adapter 20 of FIG. 1. The central server 60 may be configured as a special purpose computing device that is part of a geofencing service provider. As used herein the term geofencing refers to a virtual geographic or spatial boundary that enables software to trigger a functional response when a participating device (e.g., a vehicle) enters or leaves a particular area (e.g., safety zone).

The network 50 may be any suitable communication network or combination of networks, such as a local area network (LAN), a general wide area network (WAN), and/or a public network (e.g., the Internet). The participant devices 62, 64 may include components of the computing device 12, and may be a desktop computer, laptop computer, tablet computer, smartphone, personal wearable device (e.g., fitness tracker), a bicycle computer, a computing device of a vehicle or other types of IoT devices, for example. The vehicle 66 may be in the form of a commercially available vehicle including a computing device having components of the computing device 12. While the participant device 62, 64 may be in the form of a vehicle (e.g., vehicle 66), the term participant device herein is intended to be inclusive of a plurality of participant devices, including personal mobile devices (e.g., hand-held or small computing devices which are not vehicles, such as personal wearable devices, smartphones, PDAs and the like) and vehicles (e.g., cars, trucks, etc.). When the term participant device is utilized herein with respect to a vehicle, it should be understood that the vehicle of a first user (e.g., participant device 62) is distinguished from a vehicle of a second user (e.g., vehicle 66). The remote server 68 may be in the form of any available remote server 68, and may include components of the computing device 12. In embodiments, the remote server 68 is a weather server providing third party weather data (e.g., weather conditions) to the central server 60.

Still referring to FIG. 2, the central server 60 may include one or more program modules (e.g., program module 42 of FIG. 1) executed by the central server 60 and configured to perform one or more of the functions described herein. In embodiments, the central server 60 includes a communication module 70 configured to send and receive data to/from one or more of the participant devices 62, 64, the vehicle 66, and the remote server 68. In aspects, the communication module 70 is configured to receive user profile data from the participant devices 62, 64, and save the user profile data in a user profile database 72.

In embodiments, the central server 60 includes a safety module 74 configure to receive real-time safety data from the participant devices 62, 64 and the remote server 68, and saves the real-time safety data in the safety database 76. The safety module 74 may also receive driving event data from the vehicle 66, and save the driving event data in the safety database 76. In embodiments, the safety module 74 determines a safety zone for a user (e.g., a geofence) based on the safety data, driving event data received, user profile data and rules in a rules database 78; determines when a vehicle is entering the safety zone; and dynamically determines speed limits for the vehicle based on received data and rules in the rules database 78. The rules database 78 may include look-up tables or other data configurations enabling the central server 60 to determine safety zones around participants and target speeds for nearby vehicles based on user safety profiles and/or real-time safety data. In central-server-based embodiments, the safety module 74 sends safety information to the vehicle with instructions for performing a function (e.g., displaying a target speed to a driver, automatically decelerating the vehicle, etc.). In participant-device-based embodiments, the safety module 74 sends a safety notification to a participant device, with instructions for broadcasting a safety signal (e.g., utilizing Bluetooth, radio frequency identification (RFID) system, etc.). In embodiments, the safety module 74 receives driving pattern data of the vehicle over time and saves the driving pattern data in the user profile database 72 as part of a driver's user safety profile.

With continued reference to FIG. 2, the participant devices 62, 64 may include one or more program modules (e.g., program module 42 of FIG. 1) executed by the respective participant devices 62, 64 and configured to perform one or more of the functions described herein. In embodiments, the participant devices 62, 64 include respective communication modules 80 and 82 configured to send and receive data to/from the central server 60. In embodiments, the participant devices 62, 64 include respective GPS modules 84, 86 configured to determine a location of the respective participant devices 62, 64 and communicate the location to the central server 60. The participant devices 62, 64 may include respective user monitoring modules 88, 90 configured to obtain data regarding parameters of the user, such as heartrate, rate or type of activity of the user, etc. In participant-device-based embodiments, the participant device 64 may include a beacon module 92 configured to generate and broadcast a signal (Bluetooth, RFID, radio, etc.) that may be detected by one or more sensors of a nearby vehicle.

Still referring to FIG. 2, the vehicle 66 may include one or more program modules (e.g., program module 42 of FIG. 1) executed by the vehicle 66 and configured to perform one or more of the functions described herein. In embodiments, the vehicle 66 includes a communication module 94 configured to send and receive data to/from the central server 60. In central-server-based embodiments, the vehicle 66 includes a safety module 96 configured to receive safety information from the central server 60 and implement functions based on the safety information. For example, the safety module 96 may receive safety information from the central server 60 indicating that a target speed for the vehicle should be displayed to a user via a display 98. The display 98 may be in the form of a heads-up display, digital display, or other available type of display for use in a vehicle. In participant-device-based embodiments, the vehicle 66 may include a sensor module 100 configure to receive data from one or more sensors of the vehicle, including data indicating that the vehicle has entered a safety zone based on detecting a broadcast of a participant device 64.

In embodiments, separate components shown in FIG. 2 may be integrated into a single computing component or module. Additionally, or alternatively, a single component may be implemented as multiple computing components or modules. Moreover, the quantity of devices and/or networks in the environment of FIG. 2 is not limited to what is shown. In practice, the environment may include additional devices and/or networks; fewer devices and/or networks; different devices and/or networks; or differently arranged devices and/or networks than illustrated in FIG. 2.

Figure 3:
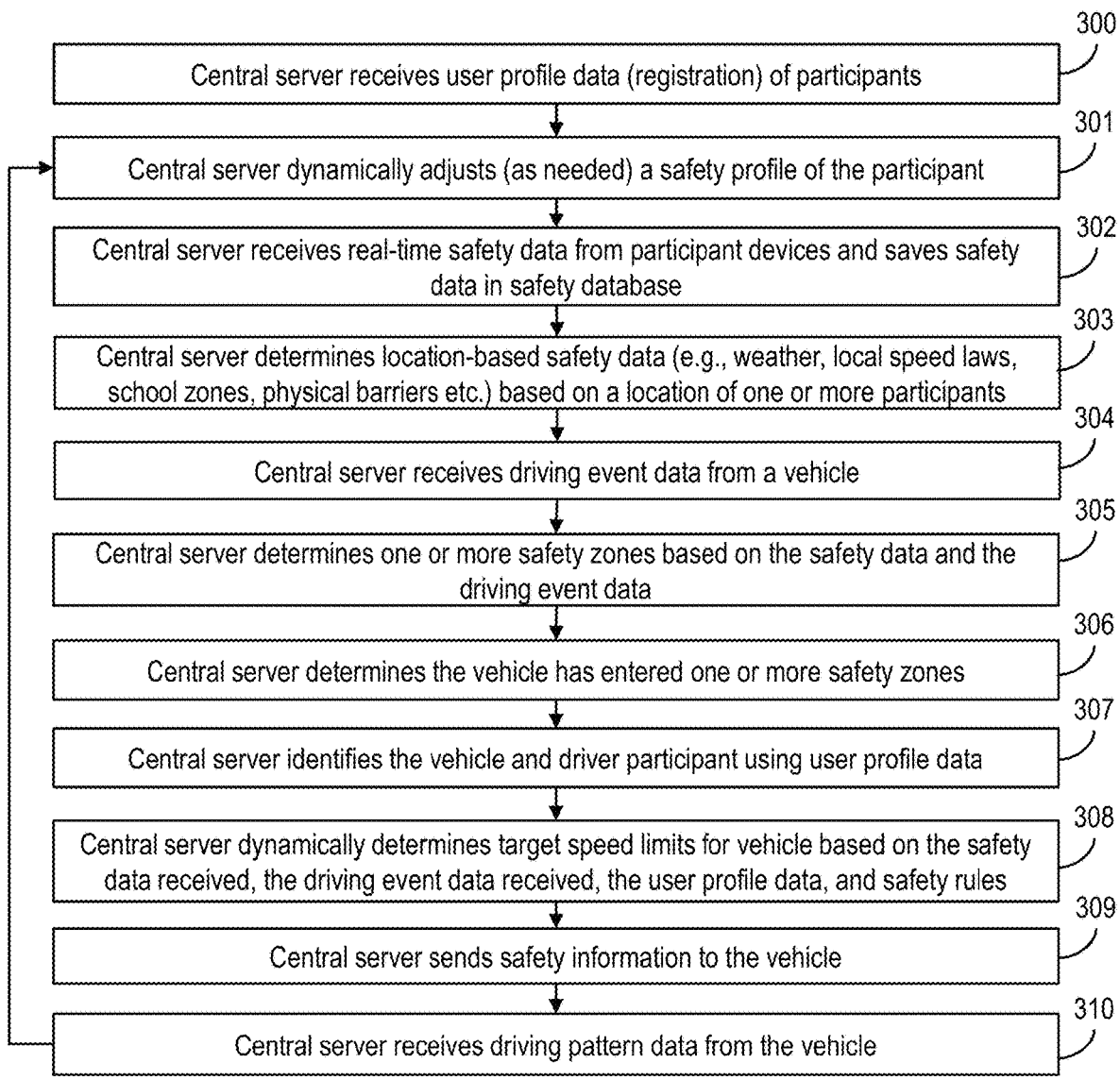
FIG. 3 shows a flowchart of steps of a central-server-based method from the perspective of the central-server in accordance with aspects of the invention.

FIG. 3 shows a flowchart of a central-server-based method in accordance with aspects of the invention. Steps of the method of FIG. 3 may be performed in the environment illustrated in FIG. 2, and are described with reference to elements shown in FIG. 2.

At step 300, a central server 60 receives user profile data of participants. In embodiments, the communication module 70 of the central server 60 receives user profile data from one or more participant devices (e.g., participant devices 62, 64) and user profile data from one or more drivers of vehicles (e.g., vehicle 66). User profile data may include, for example, a name of the user, age of user, user-configured safety parameters, type of device or vehicle (e.g., make and model of the participant device 62 or vehicle 66, bicycle), a type of user utilizing a participant device (e.g., child, animal, adult), user driving pattern data, a potential speed of a participant (e.g., predetermined maximum speed of a child, animal or adult), or other information useful in the development of a user safety profile for a participant. In embodiments, the central server 60 utilizes the user profile data to build safety profiles for participants, and saves the user profile data and/or safety profiles of the participants in the user profile database 72. User profile data may be received at the central server 60 in accordance with a user registration process.

At step 301, the central server 60 dynamically adjusts (as needed) a safety profile of the participant. In embodiments, the central server 60 continuously or periodically updates the safety profile of participants as necessary based on the incoming user profile data. In embodiments, the central server 60 updates safety profiles of a driver based on driving pattern data received in accordance with step 310, discussed in more detail below.

At step 302, the central server 60 receives real-time safety data from one or more participant devices (e.g., participant devices 62, 64). In embodiments, the safety module 74 of the central server 60 receives real-time safety data from the participant devices 62 and 64 and saves the real-time safety data in the safety database 76. The real-time safety data may include, for example, a location of a user (e.g., location of the participant device 62), biophysical data of the user (e.g., heartrate), acceleration or speed of the user (e.g., acceleration of the participant device 62), or other data regarding the status of the user. In embodiments, the real-time safety data includes GPS location data from GPS modules 84, 86 of participant devices 62, 64.

At step 303, the central server 60 determines location-based safety data, based on the respective locations of one or more participants. In embodiments, the safety module 74 of the central server 60 obtains location-based safety data based on a location of a user received at step 302. Examples of location-based safety data include local weather conditions, local speed laws, school zones, data regarding one or more physical structures, established geofences (e.g., a geofence around a school), zoning laws, traffic laws, speed recommendations, speed limits, or other safety data related to the location of the participant.

At step 304, the central server 60 receives driving event data from the vehicle 66. In embodiments, the safety module 74 receives real-time driving event data from a plurality of vehicles (e.g., vehicle 66), and saves the driving event data in the safety database 76. Driving event data may include, for example, a speed of the vehicle, acceleration or deceleration of the vehicle, a location of the vehicle, direction of travel (e.g., vehicle backing up) or other data related to the user of vehicle during a driving event. In aspects, the central server begins recording the driving event data of the vehicle 66 after an initiating event has occurred, such as the vehicle reaching a predetermined threshold speed.

At step 305, the central server 60 determines one or more safety zones for one or more participants based on the safety data received at steps 302 and 303 of FIG. 3. The term safety zone as used herein refers to a spatial safety zone defining a physical or geographic space. In embodiments, the safety module 74 of the central server 60 determines one or more safety zones based on the safety data and user safety profile. In aspects, the safety module 74 determines a type of user of the participant device 62 based on the user safety profile (e.g., the user is a child, an adult, or an animal). For example, the safety module 74 may define a 74-foot diameter safety zone extending outward from the participant device 62 when a vehicle (e.g., vehicle 66) approaches a stationary pedestrian (user of the participant device 62) at a speed of 20 miles per hour (MPH), based on rules in the rules database 78 indicating that a vehicle speed of 20 MPH requires 64 feet to stop. In another example, the safety module 74 may determine that a child participant has a potential speed X (e.g., maximum potential speed) based on the user safety profile of the child, and may determine that a spatial safety zone of 40 feet is required to maximize safety of the child based on a location of the child with respect to a nearby vehicle, using rules in the rules database 78. In embodiments, the central server 60 determines an initial spatial safety zone having a first size based on a first set of real-time safety data; determines that data regarding one or more physical structures indicates a physical barrier between the user and the vehicle 66; and determines a final spatial safety zone having a second size smaller than the first size based on the location of the physical barrier between the user and the remote vehicle.

At step 306, the central server 60 determines that a vehicle (e.g., the vehicle 66) has entered one or more safety zones. In aspects, the safety module 74 determines that the vehicle 66 has entered a safety zone determined at step 305, based on real-time location information received from the vehicle 66 and the participant device 62. In aspects, the central server 60 may determine that the vehicle 66 has entered a safety zone, when sensors of the vehicle 66 sense that the vehicle has entered a safety zone or geofence, and sends a signal to the central server 60 indicating that the vehicle 66 has entered the safety zone or geofence.

At step 307, the central server 60 identifies the vehicle 66 of step 306 and the associated driver participant (driver of the vehicle 66) based on user profile data in the user profile database 72. In embodiments, the safety module 74 of the central server 60 identifies user safety data of the driver participant.

At step 308, the central server 60 dynamically determines a target speed limit for the vehicle 66 based on the safety data received at step 302, the driving event data received at step 304, user safety data of the participants (e.g., user of the participant device 62 and driver of the vehicle 66) and safety rules in the rules database 78. In embodiments, the safety module 74 of the central server 60 determines the target speed limit of the vehicle 66 in response to step 306. The target speed limit may be a speed that is slower than the actual speed of the vehicle 66, as determined from real-time driving event data received at step 304. For example, the central server 60 may determine, based on a speed and location of the participant device 62, a speed and location of the vehicle 66, a local speed limit of 20 MPH, and weather data indicating that it is raining at the location of the participant device 64, that a target speed for the vehicle should be 15 MPH.

At step 309, the central server 60 sends safety information to the vehicle 66. In embodiments, the communication module 70 of the central server sends safety information to the communication module 94 of the vehicle 66 via the network 50. The safety information may comprise one or more instructions for the vehicle 66 to initiate one or more functions. By way of example, the safety information may comprise instructions for the vehicle 66 to display the target vehicle speed (determined at step 308) to the driver of the vehicle 66 via the display 98. In another example, the safety information may comprise instructions for the vehicle 66 to automatically change an actual speed of the vehicle 66 to match the target vehicle speed. In embodiments the central server 60 may implement step 309 based on step 308. For example, the central server 60 may send safety information to the vehicle 66 when a speed of the vehicle 66 exceeds the target speed determined at step 308. In embodiments, the safety information may include information regarding a participant device in the form of another vehicle, such as an indication that the other vehicle is on the side of a road, etc.

At step 310, the central server 60 receives driving pattern data from the vehicle 66. The driving pattern data may be any data regarding driving patterns of a driver, including acceleration/deceleration data, reaction time of the driver, distance required for the vehicle 66 to come to a complete stop, etc. Driving pattern data may be received at the central server 60 on a continuous or periodic basis. In accordance with step 301 discussed above, the central server 60 may adjust a safety profile of the driver participant as needed based on the driving pattern data collected at step 310.

It should be understood that certain steps of FIG. 3 may be performed simultaneously with other steps of FIG. 3, and that steps may be performed in real-time or near-real time as data is received and processed. For example, the central server 60 may simultaneously receive real-time safety data from the participant device 62, driving event data from the vehicle 66, and location-based safety data (weather data) from the remote server 68. Moreover, steps of FIG. 3 may be performed on a continuous basis, such that safety zones determined by central server 60 may change in real-time based on incoming data, and safety information sent to vehicles may likewise be continuously updated or changed in real-time based on the incoming data.

Figure 4:
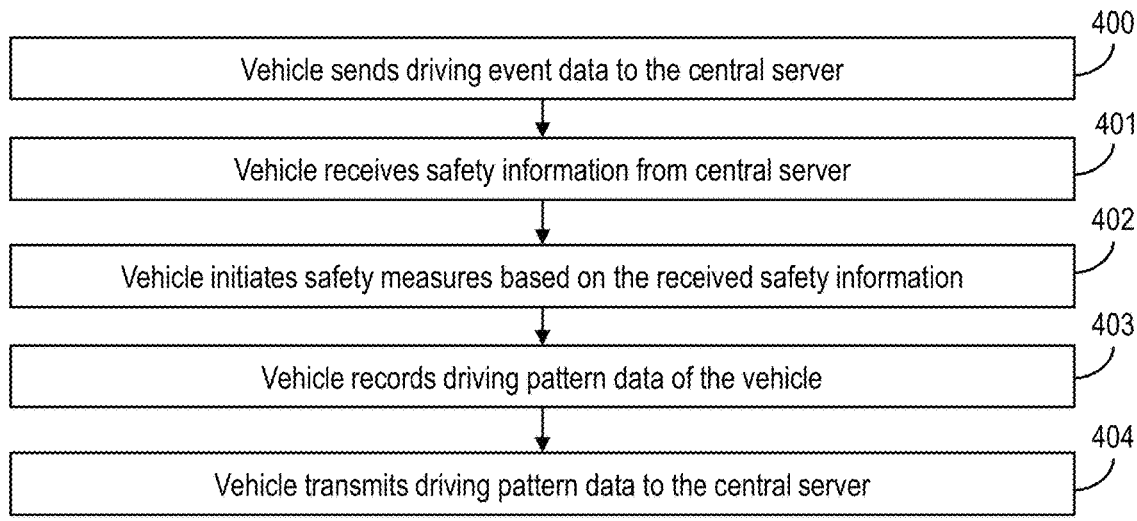
FIG. 4 shows a flowchart of steps of the central-server-based method from the perspective of a vehicle in accordance with aspects of the invention.

FIG. 4 shows a flowchart of steps performed by a vehicle in accordance with the central-server-based method illustrated in FIG. 3. Steps of the method of FIG. 4 may be performed in the environment illustrated in FIG. 2, and are described with reference to elements shown in FIG. 2.

In step 400, the vehicle 66 sends driving event data to the central server 60. In embodiments, the communication module 94 of the vehicle 66 sends driving event data to the communication module 70 of the central server 60 via the network 50.

In step 401, the vehicle 66 receives safety information from the central server 60. In embodiments, the communication module 94 of the vehicle 66 receives the safety information (i.e., safety information from step 309 of FIG. 3) from the communication module 70 of the central server 60 and sends the safety information to the safety module 96 for processing.

In step 402, the vehicle 66 initiates safety measures based on the safety information received at step 401. In embodiments, the safety module 96 of the vehicle 66 initiates the safety measures in response to receiving the safety information. For example, the safety module 96 may cause a target speed or a warning to be displayed by the display 98 of the vehicle 66.

At step 403, the vehicle 66 records driving pattern data of the vehicle. In embodiments, the safety module 96 monitors driving parameters and records driving pattern data in a database of the vehicle 66 (not shown). Driving pattern data may be collected continuously or periodically. Available vehicular data gathering systems may be utilized in the implementation of step 403.

At step 404, the vehicle 66 transmits the driving pattern data recorded at step 403 to the central server 60. In embodiments the safety module 96 sends the driving pattern data to the central server via the communication module 94 of the vehicle 66. The driving pattern data may be sent to the central server 60 by the vehicle 66 on a continuous or periodic basis.

Figure 5:
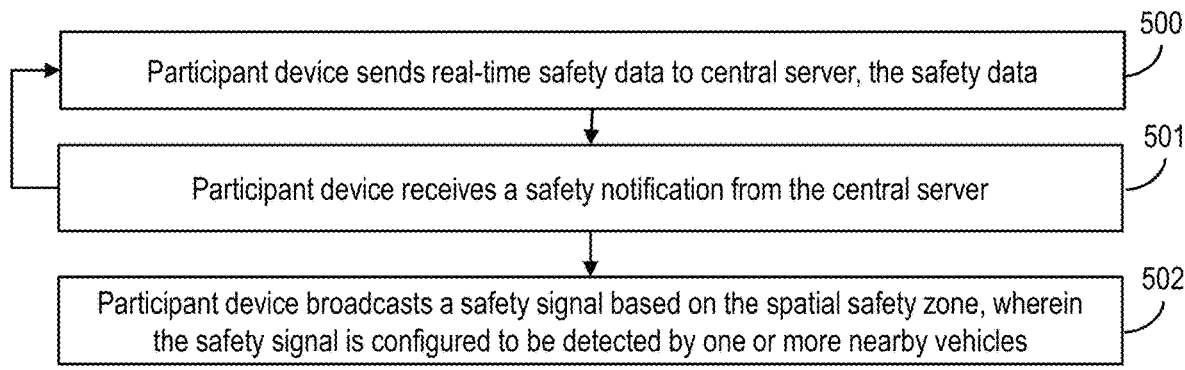
FIG. 5 shows a flowchart of steps of the participant-device-based method from the perspective of the participant device in accordance with aspects of the invention.

FIG. 5 shows a flowchart of steps performed in accordance with a participant-device-based method of the invention. Steps of the method of FIG. 5 may be performed in the environment illustrated in FIG. 2, and are described with reference to elements shown in FIG. 2.

At step 500, the participant device 64 sends real-time safety data to the central server 60. In embodiments, the communication module 82 of the participant device 64 sends real-time safety data to the communication module 70 of the central server 60 via the network 50. The real-time safety data may include, for example, a location of a user (e.g., location of the participant device 64 obtained by the GPS module 86), biophysical information of the user (e.g., heart-rate data obtained by the user monitoring module 90), acceleration or speed of the user (e.g., acceleration of the participant device 64 obtained by the user monitoring module 90), or other data regarding the status of the user.

At step 501, the participant device 64 receives a safety notification from the central server 60. In embodiments, the safety notification includes a defined spatial safety zone (i.e., the safety zone determined at step 305 of FIG. 3). The safety notification may contain instructions for the participant device 64 to initiate safety measures. For example, the safety notification may include instructions for the participant device 64 to transmit or broadcast a signal representative of the defined spatial safety zone (e.g., broadcast a safety signal having a radius or range of at least 40 feet).

At step 502, the participant device 64 broadcasts or transmits a safety signal in response to the safety notification received at step 501. In embodiments, the beacon module 92 of the participant device 64 broadcasts or transmits the safety signal. For example, the beacon module 92 may transmit a safety signal having a range of at least 40 feet in response to the safety notification received in accordance with step 501. In embodiments, the safety signal is configured to be detected by one or more sensors of a vehicle (e.g., Bluetooth sensors). The safety signal may comprise one or more instructions for the vehicle 66 to initiate safety measures. For example, the safety signal may include instructions to meet a target vehicular speed limit, or may include instructions to display a warning or a notification to a driver of the vehicle 66 to slow down or meet the target vehicular speed limit. In aspects, the safety signal comprises an alert regarding a status of the user (e.g., user in distress, user in road, etc.).

Figure 6:
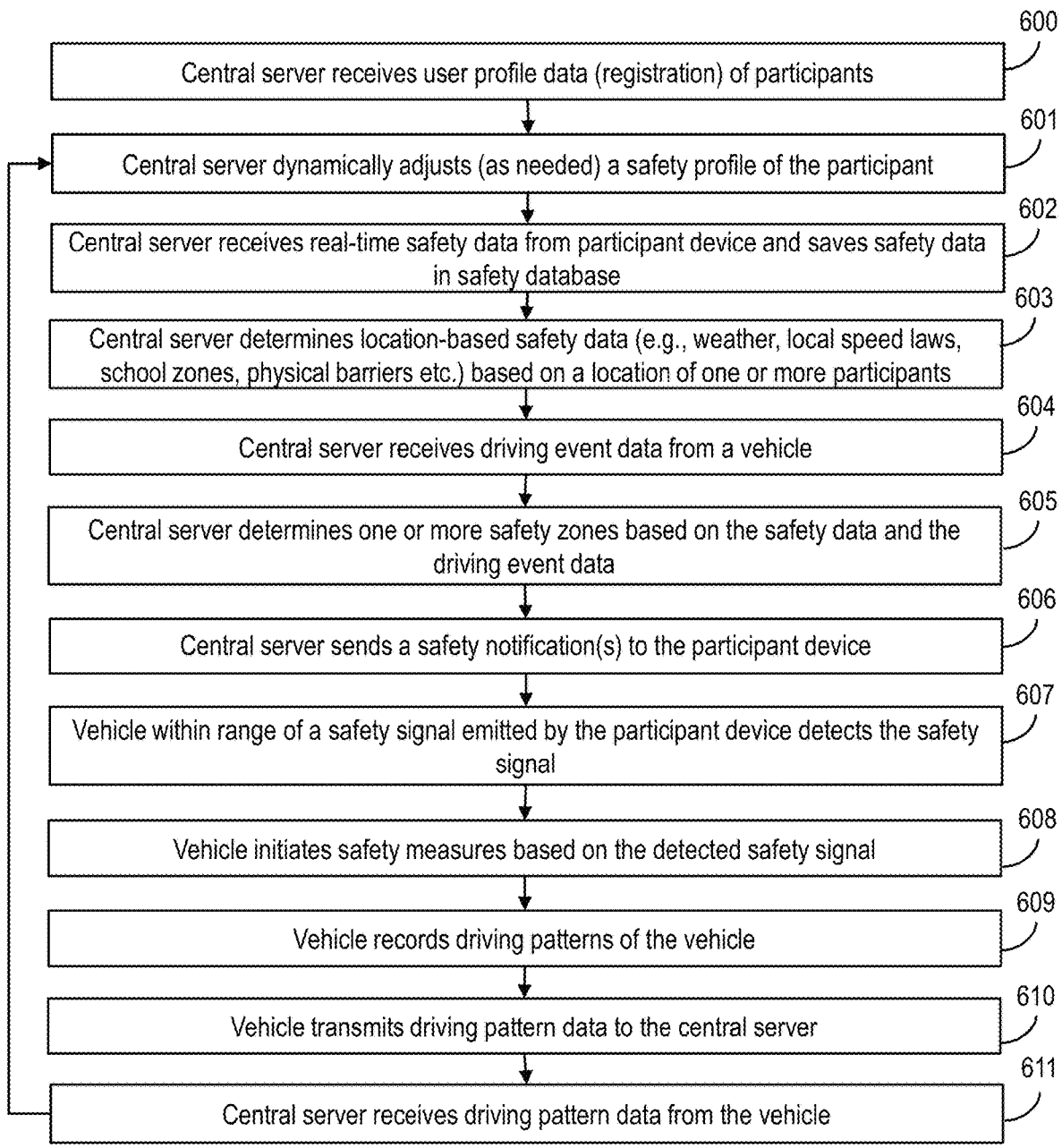
FIG. 6 shows a flowchart of steps of the participant-device-based method from the perspective of a central server and a vehicle in accordance with aspects of the invention.

FIG. 6 shows a flowchart of steps performed by a central server and a vehicle in accordance with the participant-device-based method of FIG. 5. Steps of the method of FIG. 6 may be performed in the environment illustrated in FIG. 2, and are described with reference to elements shown in FIG. 2.

Steps 600-605 of FIG. 6 are the same as steps 300-305 of FIG. 3, but with reference to the participant device 64. As such, steps 600-605 are not discussed herein.

At step 606, the central server 60 sends a safety notification to the participant device 64, wherein the safety notification is received at the participant device 64 in accordance with step 501 of FIG. 5. As discussed above with respect to FIG. 5, the safety notification may include a defined spatial safety zone, and/or instructions for the participant device 64 to initiate safety measures. For example, the safety notification may include instructions for the participant device 64 to transmit or broadcast a signal representative of the defined spatial safety zone (e.g., broadcast a safety signal having a radius or range of at least 40 feet). In embodiments, the safety notification includes a target speed determined by the central server 60 based on the safety data received at step 602, the driving event data received at step 604, user safety data of the participants (e.g., user of the participant device 64 and driver of the vehicle 66) and safety rules in the rules database 78.

At step 607, the vehicle 66 within range of the safety signal emitted by the participant device 64 (in accordance with step 502 of FIG. 5) detects the safety signal. In embodiments, the sensor module 100 of the vehicle 66 receives data from one or more sensors of the vehicle 66 indicating that the vehicle 66 has detected the safety signal being emitted by the participant device 64.

At step 608, the vehicle 66 initiates safety measures based on the safety signal detected at step 607. In embodiments, the safety module 96 of the vehicle 66 processes the safety signal and determines safety measures to initiate based on the signal. For example, the safety module 96 may cause the vehicle 66 to display a target vehicle speed to the driver of the vehicle 66 via the display 98. In another example, the safety module 96 may cause the vehicle 66 to automatically change an actual speed of the vehicle 66 to match the target vehicle speed.

At step 609, the vehicle 66 records driving pattern data of the vehicle 66. The driving pattern data may be any data regarding driving patterns of a driver, including acceleration/deceleration data, reaction time of the driver, distance required for the vehicle 66 to come to a complete stop, etc. Driving pattern data may be recorded on a continuous or periodic basis, and may be recorded in response to a triggering event (e.g., the vehicle 66 meeting or exceeding a target speed).

At step 610, the vehicle 66 transmits the driving pattern data of the vehicle 66 to the central server. Driving pattern data may be sent to the central server 60 by the vehicle 66 on a continuous or periodic basis.

At step 611, the central server receives the driving pattern data of sent at step 610. In accordance with step 601, the central server 60 may adjust a safety profile of the driver participant as needed based on the driving pattern data collected at step 611.

It should be understood that certain steps of FIG. 6 may be performed simultaneously with other steps of FIG. 6, and that steps may be performed in real-time or near-real time as data is received and processed. For example, the central server 60 may simultaneously receive real-time safety data from the participant device 64, driving event data from the vehicle 66, and location-based safety data (weather data) from the remote server 68. Moreover, steps of FIG. 6 may be performed on a continuous basis, such that safety zones determined by central server 60 may change in real-time based on incoming data, and safety notifications sent to participant devices (e.g., participant device 64) may likewise be continuously updated or changed in real-time based on the incoming data.

Figure 7:
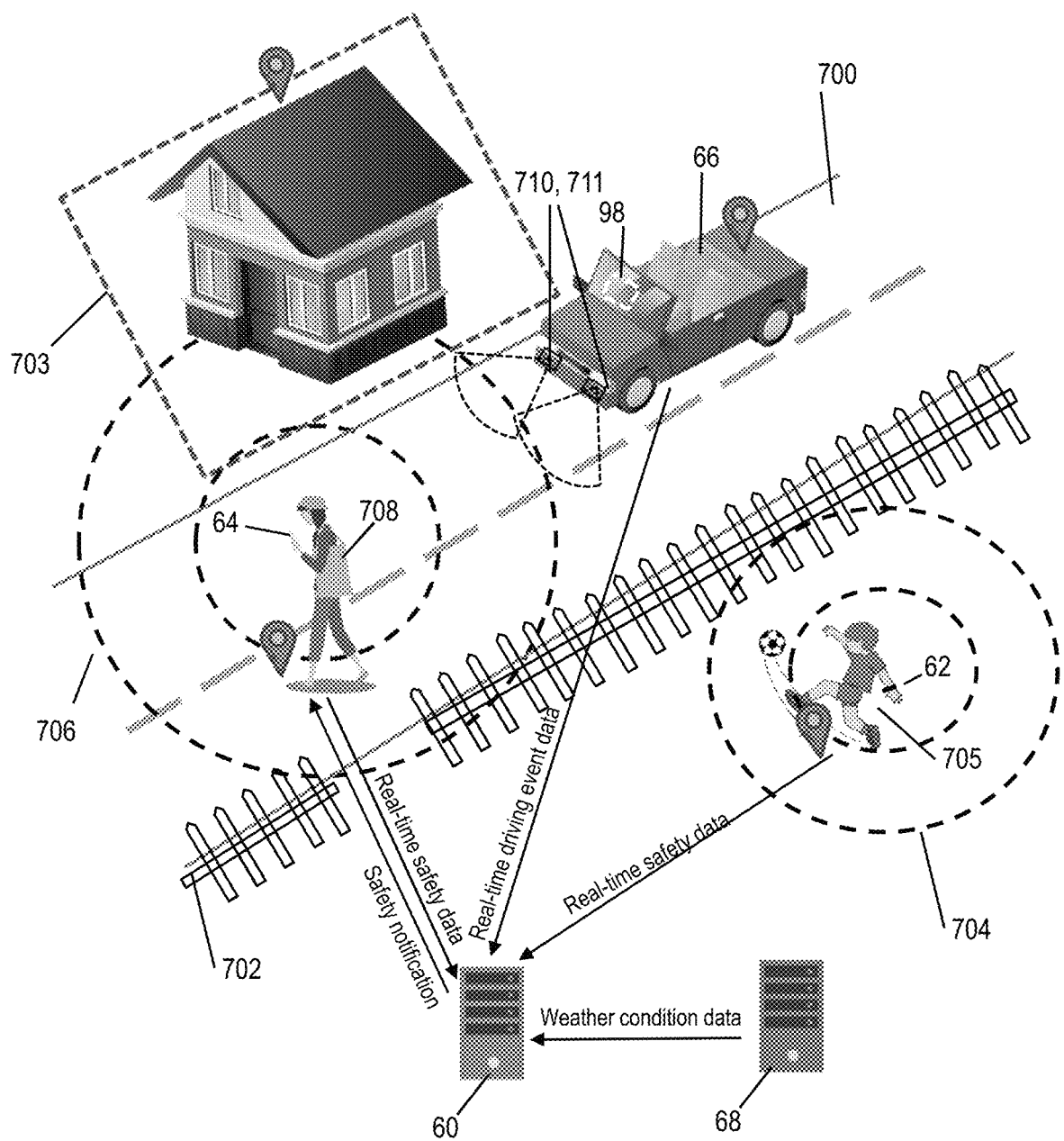
FIG. 7 illustrates exemplary use scenarios of embodiments of the invention.

FIG. 7 illustrates exemplary scenarios in accordance with embodiments of the invention. Steps of the scenarios discussed below may be performed in the environment illustrated in FIG. 2, and are described with reference to elements shown in FIG. 2.

A first exemplary scenario will now be discussed with reference to FIGS. 3 and 7. In accordance with step 302 of FIG. 3, real-time safety data is sent from the participant device 62 to the central server 60. In this scenario, the real-time safety data includes a location of the participant device 62. Further, driving event data is sent from the vehicle 66 to the central server 60 in accordance with step 304 of FIG. 3. The central server 60 also obtains weather condition data from the remote server 68 for conditions at the location of the participant device 62 in accordance with step 303 of FIG. 3. The central server 60 further looks up speed limits for the location of the participant device 62 in the rules database 78 (depicted in FIG. 2), and determines that the speed limit for the road 700 is 20 MPH. The central server also determines that a fence 702 is between a road 700 and the participant device 62 (utilizing existing image recognition techniques), and a school zone 703 is present (e.g., utilizing information from a map of the location).

In accordance with step 305 of FIG. 3, the central server 60 determines an initial safety zone (not shown) around the participant device is 60 feet based on the participant device being located near a school zone 703, the road 700 with a speed limit of 20 MPH, and the user safety profile, which indicates that default child safety rules should apply for the participant device 62 (e.g., the child has a maximum potential speed of X). However, in accordance with this scenario, a second safety zone 704 around the participant device 62 is determined to be 10 feet based on the fact that a safety barrier (the fence 702) is located between the road 700 and the participant device 62. In other words, the fence 702 is a mitigating factor that causes the central server 60 to adjust the safety zone from the initial safety zone (not shown), to the smaller, second safety zone 704. This scenario reflects the fact that a child participant 705 is in greater danger if the child 705 could potentially run into the road 700, and is in less danger if the child 705 is prevented from running into the road by a barrier (e.g., the fence 702). In this scenario, the vehicle 66 does not enter the second safety zone 704 of the participant device 62, and thus, no safety information is sent from the central server 60 to the vehicle 66 regarding the participant device 62 in accordance with step 309 of FIG. 3.

A second exemplary scenario will now be discussed with reference to FIGS. 5-7. In accordance with step 602 of FIG. 2, real-time safety data is sent from the participant device 64 to the central server 60. In this scenario, the real-time safety data includes a location of the participant device 64. Further, driving event data is sent from the vehicle 66 to the central server 60 in accordance with step 604 of FIG. 6. The central server 60 also obtains weather condition data from the remote server 68 for conditions at the location of the participant device 64 in accordance with step 603 of FIG. 6. The central server 60 further looks up speed limits for the location of the participant device 64 in the rules database 78 (depicted in FIG. 2), and determines that the speed limit for the road 700 is 20 MPH.

Still referring to FIGS. 5-7, in accordance with step 605 of FIG. 6, the central server 60 determines a safety zone 706 around the participant device 64 is 64 feet based on the location of the participant device 64 in the road, the speed limit of 20 MPH, the weather condition data which indicates a dry, sunny day, and the user safety profile of the participant 708, which indicates that default safety rules should apply for the participant device 64. In accordance with step 606 of FIG. 6, the central server 60 sends a safety notification to the participant device 64 with instructions for the participant device 64 to transmits a safety signal having a range of at least 64 feet, the safety signal comprising instructions for a vehicle to "use caution". In accordance with steps 501 and 502 of FIG. 5, the participant device 64 receives the safety notification from the central server 60 and automatically broadcasts the safety signal indicating that any vehicle within range of the broadcast should "use caution". In this scenario, sensors 710 and 711 of the vehicle 66 detect the safety signal (represented at 706), and a safety module 96 of the vehicle 66 automatically displays a warning to the driver via the display 98 to "use caution", in accordance with steps 607 and 608 of FIG. 6.

Based on a continuous feed of real-time safety data from the participant device 64 to the central server 60, the central server 60 recognizes that the participant device 64 has stopped in the road 700, and issues a second safety notification to the participant device 64, including instructions to broadcast a second safety signal warning any nearby cars to "stop, pedestrian in road ahead" in accordance with step 606 of FIG. 6. In this scenario, the participant device 64 automatically broadcasts the second safety signal upon receipt of the second safety notification in accordance with step 502 of FIG. 5, and the vehicle 66 detects the safety signal and initiates safety measure in accordance with steps 607 and 608 of FIG. 6. In this scenario, the vehicle 66 displays the message "stop, pedestrian on the road ahead" on the display 98 in accordance with step 608 of FIG. 6.

In embodiments, a service provider could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still another embodiment, the invention provides a computer-implemented method for dynamically defining a safety zone around a user. In this case, a computer infrastructure, such as computer system 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
   receiving, by a computing device, real-time safety data including a location of a remote participant device of a user;
   receiving, by the computing device, real-time driving event data from a remote vehicle;
   determining, by the computing device, a spatial safety zone about the participant device of the user based on the real-time safety data and the real-time driving event data;
   determining, by the computing device, that the remote vehicle has entered the spatial safety zone; and
   sending, by the computer device, safety information regarding the user to the remote vehicle based on the remote vehicle entering the spatial safety zone.

2. The method of claim 1, wherein the real-time safety data includes a speed at which the remote participant device is traveling, and the real-time driving event data includes a speed at which the remote vehicle is traveling.

3. The method of claim 2, further comprising determining, by the computing device, a target speed limit for the remote vehicle based on the real-time safety data and the real-time driving event data, wherein the safety information includes the target speed limit for the remote vehicle.

4. The method of claim 3, wherein the target speed limit is a dynamically changing target speed limit based on the real-time safety data and the real-time driving event data, and the safety information is sent to the remote vehicle in real-time.

5. The method of claim 3, further comprising:
   receiving, by the computing device, user profile data of a driver of the remote vehicle and generating a user safety profile for the driver;
   receiving, by the computing device, historic driving pattern data regarding driving patterns of the driver; and
   dynamically adjusting, by the computing device, the user safety profile of the driver based on the driving pattern data, wherein the target speed limit is further based on the user safety profile of the driver.

6. The method of claim 1, wherein the safety information includes instructions to the remote vehicle to automatically initiate safety measure of the remote vehicle.

7. The method of claim 1, wherein a size of the spatial safety zone is adjusted dynamically based on the real-time safety data and the real-time driving event data.

8. The method of claim 7, wherein the real-time safety data comprises one or more selected from the group consisting of: biophysical data of the user; and established geofences.

9. The method of claim 7, wherein the real-time safety data includes data regarding one or more physical structures, wherein the determining the spatial safety zone based on the safety data comprises:
- determining an initial spatial safety zone having a first size based on a first set of real-time safety data;
- determining that the data regarding one or more physical structures indicates a physical barrier between the user and the remote vehicle; and
- determining a final spatial safety zone having a second size smaller than the first size based on the physical barrier between the user and the remote vehicle.

10. The method of claim 1, wherein the real-time safety data includes data indicating that the user is in distress, and the safety information regarding the user comprises a warning configured to be displayed to a driver of the remote vehicle warning the driver to slow down.

11. The method of claim 1, wherein the user is a pedestrian and the remote participant device is a smartphone or personal wearable device.

12. A computer program product for dynamically defining a safety zone around a user, the computer program product comprising a computer readable storage medium having program instructions embodied therewith, the program instructions executable by a computing device to cause the computing device to:
- send real-time safety data regarding a participant device to a remote central server, the real-time safety data including a location of the participant device;
- receive a safety notification from the central server, the safety notification including a defined spatial safety zone about the participant device; and
- broadcast a safety signal based on the safety notification, wherein the safety signal is configured to be detected by one or more sensors of a vehicle.

13. The computer program product of claim 12, wherein the safety signal comprises instructions to cause the vehicle to automatically implement safety measures.

14. The computer program product of claim 12, wherein the real-time safety data comprises biophysical data of a user of the participant device, and the safety signal comprises an alert regarding a status of the user.

15. A system for dynamically defining a safety zone around a user, comprising:
- a CPU, a computer readable memory and a computer readable storage medium associated with a computing device;
- program instructions to receive real-time safety data including a location of a remote participant device of a user;
- program instructions to receive real-time driving event data from a remote vehicle, the real-time driving event data including a speed of the remote vehicle;
- program instructions to determine a spatial safety zone based on the real-time safety data and the real-time driving event data; and
- program instructions to send a safety notification to the participant device, the safety notification causing a safety signal to be broadcast from the participant device based on the spatial safety zone,
- wherein the program instructions are stored on the computer readable storage medium for execution by the CPU via the computer readable memory.

16. The system of claim 15, further comprising program instructions to determine a target speed limit for the remote vehicle based on the real-time safety data and the real-time driving event data, wherein the safety notification includes instructions to broadcast the target speed limit.

17. The system of claim 16, wherein the target speed limit is a dynamically changing target speed limit based on the real-time safety data and the real-time driving event data, and the safety notification is updated as the target speed limit changes.

18. The system of claim 15, wherein the safety notification includes instructions to the remote vehicle to automatically initiate safety measure of the remote vehicle.

19. The system of claim 15, wherein a size of the spatial safety zone is adjusted dynamically based on the real-time safety data and the real-time driving event data.

20. The system of claim 15, wherein the real-time safety data comprises one or more selected from the group consisting of: a speed at which the remote participant device is traveling; acceleration or deceleration of the remote participant device; data regarding one or more physical structures; weather conditions; biophysical data of the user; established geofences; predefined zoning laws; predefined traffic laws; predetermined speed recommendations; and predefined speed limits.

* * * * *